United States Patent [19]
Co et al.

[11] Patent Number: 5,714,350
[45] Date of Patent: Feb. 3, 1998

[54] INCREASING ANTIBODY AFFINITY BY ALTERING GLYCOSYLATION IN THE IMMUNOGLOBULIN VARIABLE REGION

[75] Inventors: Man Sung Co, Cupertino, Calif.; David A. Scheinberg, New York, N.Y.; Cary L. Queen, Los Altos, Calif.

[73] Assignees: Protein Design Labs, Inc.; Sloan-Kettering Cancer Center, both of Mountain View, Calif.

[21] Appl. No.: 372,262

[22] Filed: Jan. 13, 1995

Related U.S. Application Data

[63] Continuation of Ser. No. 850,354, Mar. 9, 1992, abandoned.

[51] Int. Cl.[6] .......... A61K 39/395; C12P 21/08; C12P 21/04; C12N 15/13
[52] U.S. Cl. .......... 435/69.6; 435/70.21; 435/71.1; 435/240.27; 435/172.1; 424/133.1; 530/387.3; 935/49; 935/50
[58] Field of Search .......... 435/69.6, 172.1, 435/70.21, 71.1, 240.27; 530/387.1, 387.3; 424/133.1; 935/49, 50

[56] References Cited

FOREIGN PATENT DOCUMENTS 9007861   7/1990   WIPO .

OTHER PUBLICATIONS

Zoller et al. Methods in Immunology 1983 vol. 100 p. 469.

Wright et al. Embo 10(10) p. 2717, 1991.

Waldmann Science vol. 252, p. 1657, 1991.

Co et al. Journal of Immunology 143(8) 1989.

Hird et al Genes & Cancer Chapter 17 183–198, 1990 "Immunotherapy with monocolonal antibodies".

Wallick et al. J. Exp. Medicine 168:1099, 1988.

Primary Examiner—Lila Feisee
Assistant Examiner—John Lucas
Attorney, Agent, or Firm—Townsend and Townsend and Crew, LLP

[57] ABSTRACT

The present invention provides methods for producing mutationally-altered immunoglobulins and compositions containing such mutationally-altered immunoglobulins, wherein the mutationally-altered immunoglobulins have at least one mutation that alters the pattern of glycosylation in a variable region and thereby modifies the affinity of the immunoglobulin for a preselected antigen. The methods and compositions of the invention provide immunoglobulins that possess increased affinity for antigen. Such glycosylation-altered immunoglobulins are suitable for diagnostic and therapeutic applications.

16 Claims, 3 Drawing Sheets

|  | 67 |  |  |  |  |  |  |  | 80 |  |  |  |  |  |
|---|---|---|---|---|---|---|---|---|---|---|---|---|---|---|
| CHIMERIC | Lys | Ala | Thr | Leu | Thr | Val | Asp | Asn Ser Ser | Ser | Thr | Ala | Tyr | (SEQ ID NO:5) |
| CHIMERIC - CHO | Lys | Ala | Thr | Leu | Thr | Val | Asp | Gln Ser Ser | Ser | Thr | Ala | Tyr | (SEQ ID NO:7) |
| HUMANIZED + CHO | Lys | Ala | Thr | Ile | Thr | Ala | Asp | Asn Ser Ser | Ser | Thr | Ala | Tyr | (SEQ ID NO:8) |
| HUMANIZED | Lys | Ala | Thr | Ile | Thr | Ala | Asp | Glu Ser Thr | Asn | Thr | Ala | Tyr | (SEQ ID NO:6) |

FIG. 1.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1..3
        ( D ) OTHER INFORMATION: /note= "Residue #1 is Thr or Ser; residues #2-#3 are any amino acid."

( x i ) SEQUENCE DESCRIPTION: SEQ ID NO:1:

Xaa  Xaa  Xaa  Pro
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3..4
        ( D ) OTHER INFORMATION: /note= "Xaa is any amino acid."

( x i ) SEQUENCE DESCRIPTION: SEQ ID NO:2:

Ser  Gly  Xaa  Gly
    1

( 2 ) INFORMATION FOR SEQ ID NO:3:

( i ) SEQUENCE CHARACTERISTICS:

(A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Glu Ser Thr Asn
    1

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Asn Ser Ser Ser
    1

(2) INFORMATION FOR SEQ ID NO:5:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Lys Ala Thr Leu Thr Val Asp Asn Ser Ser Ser Thr Ala Tyr
    1               5                   10

(2) INFORMATION FOR SEQ ID NO:6:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Lys Ala Thr Ile Thr Ala Asp Glu Ser Thr Asn Thr Ala Tyr
    1               5                   10

(2) INFORMATION FOR SEQ ID NO:7:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Lys Ala Thr Leu Thr Val Asp Gln Ser Ser Ser Thr Ala Tyr
    1               5                   10

(2) INFORMATION FOR SEQ ID NO:8:

(i) SEQUENCE CHARACTERISTICS:

( A ) LENGTH: 14 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:8:

Lys  Ala  Thr  Ile  Thr  Ala  Asp  Asn  Ser  Ser  Ser  Thr  Ala  Tyr
        1                 5                               10

INCREASING ANTIBODY AFFINITY BY ALTERING GLYCOSYLATION IN THE IMMUNOGLOBULIN VARIABLE REGION

This is a Continuation of application Ser. No. 07/850,354 filed Mar. 9, 1992 now abandoned.

TECHNICAL FIELD

The invention relates to mutationally altered monoclonal antibodies, methods of producing mutationally altered monoclonal antibodies, recombinant polynucleotides encoding mutationally altered immunoglobulins, methods for site-directed mutation of immunoglobulin coding sequences that alter post-translational glycosylation of immunoglobulin polypeptides, expression vectors and homologous recombination vectors for constructing and expressing mutationally altered immunoglobulins, and cells and animals that express mutationally altered immunoglobulins.

BACKGROUND

Glycosylation of immunoglobulins has been shown to have significant effects on their effector functions, structural stability, and rate of secretion from antibody-producing cells (Leatherbarrow et al., *Mol. Immunol.* 22:407 (1985)). The carbohydrate groups responsible for these properties are generally attached to the constant (C) regions of the antibodies. For example, glycosylation of IgG at asparagine 297 in the $C_H2$ domain is required for full capacity of IgG to activate the classical pathway of complement-dependent cytolysis (Tao and Morrison, *J. Immunol.* 143:2595 (1989)). Glycosylation of IgM at asparagine 402 in the $C_H3$ domain is necessary for proper assembly and cytolytic activity of the antibody (Muraoka and Shulman, *J. Immunol.* 142:695 (1989)). Removal of glycosylation sites as positions 162 and 419 in the $C_H1$ and $C_H3$ domains of an IgA antibody led to intracellular degradation and at least 90% inhibition of secretion (Taylor and Wall, *Mol. Cell. Biol.* 8:4197 (1988)).

Glycosylation of immunoglobulins in the variable (V) region has also been observed. Sox and Hood, *Proc. Natl. Acad. Sci. USA* 66:975 (1970), reported that about 20% of human antibodies are glycosylated in the V region. Glycosylation of the V domain is believed to arise from fortuitous occurrences of the N-linked glycosylation signal Asn-Xaa-Ser/Thr in the V region sequence and has not been recognized in the art as playing an important role in immunoglobulin function.

It has been reported that glycosylation at CDR2 of the heavy chain, in the antigen binding site, of a murine antibody specific for α-(1-6)dextran increases its affinity for dextran (Wallick et al., *J. Exp. Med.* 168:1099 (1988) and Wright et al., *EMBO J.* 10:2717 (1991)).

M195 is a murine IgG2a monoclonal antibody that binds CD33 antigen and has therapeutic potential for the treatment of myloid leukemia (Tanimoto et al., *Leukemia* 3:339 (1989) and Scheinberg et al., *Leukemia* 3:440 (1989)). M195 binds to early myeloid progenitor cells, some monocytes, and the cells of most myeloid leukemias, but not to the earliest hematopoietic stem cells.

The efficient cellular binding and internalization of M195 has allowed use of the radiolabeled antibody in clinical trials for acute myelogenous leukemia (AML) (Scheinberg et al., *J. Clin. Oncol.* 9:478 (1991)). The murine M195 antibody, however, does not kill leukemic cells by complement-dependent cytotoxicity with human complement, or by antibody-dependent cellular cytotoxicity with human effector cells. The human anti-mouse antibody (HAMA) response may also preclude long term use of the murine antibody in patients. To increase the effector function and reduce the immunogenicity of the M195 antibody in human patients, chiric and humanized versions of the antibody have been constructed (Co et al., *J. Immunol.* 148: 1149, (1992)). The chimetic antibody combines the murine M195 V region with a human C region, while the humanized antibody combines the complementarity determining regions (CDRs) of murine M195 with a human antibody V region framework and C region (Co et al., op.cit.). The construction and characterization of chimeric and humanized M195 antibodies of the human IgG1 isotype is described (Co et al., op.cit.).

While the production of so called "chimeric antibodies" (e.g., mouse variable regions joined to human constant regions) has proven somewhat successful in reducing the HAMA response, a significant immunogenicity problem remains. Moreover, efforts to immortalize human B-cells or generate human hybridomas capable of producing human immunoglobulins against a desired antigen have been generally unsuccessful, particularly with many important human antigens. Most recently, recombinant DNA technology has been utilized to produce immunoglobulins which have human framework regions combined with complementarity determining regions (CDR's) from a donor mouse or rat immunoglobulin (see, e.g., EPO Publication No. 0239400). These new proteins are called "reshaped" or "humanized" immunoglobulins and the process by which the donor immunoglobulin is converted into a human-like immunoglobulin by combining its CDR's with a human framework is called "humanization". Humanized antibodies are important because they bind to the same antigen as the original antibodies, but are less immunogenic when injected into humans.

However, a major problem with humanization procedures has been a loss of affinity for the antigen (Jones et al., *Nature,* 321, 522–525 (1986)), in some instances as much as 10-fold or more, especially when the antigen is a protein (Verhoeyen et al., *Science,* 239, 1534–1536 (1988)). Loss of any affinity is, of course, highly undesirable. At the least, it means that more of the humanized antibody will have to be injected into the patient, at higher cost and greater risk of adverse effects. Even more critically, an antibody with reduced affinity may have poorer biological functions, such as complement lysis, antibody-dependent cellular cytotoxicity, or virus neutralization. For example, the loss of affinity in the partially humanized antibody HuVHCAMP may have caused it to lose all ability to mediate complement lysis (see, Riechmann et al., *Nature,* 332, 323–327 (1988); Table 1).

Therefore, there exists a need in the art for immunoglobulins that have an altered affinity for antigen, particularly an increased affinity and/or increased specificity for an antigen, and, desirably, potentially lower immunogenicity and improved effector function conferred by naturally-occurring constant region glycosylation. For example, an immunoglobulin having one or more human constant region effector functions and an improved binding affinity and/or specificity characteristic of the M195 antibody variable region may eliminate the need for radiolabeling and allow repeated does in therapeutic trails. Additionally, there is a need in the art for methods that produce immunoglobulins which have improved binding affinity and/or specificity for an antigen, but which do not have significantly increased immunogenicity. Thus, there exists a need in the art for methods to increase the efficacy and reduce the required doses of immunoglobulins of therapeutic importance, and immunoglobulins produced by such methods.

SUMMARY OF THE INVENTION

This invention provides methods for producing mutated immunoglobulins, particularly mutated monoclonal antibodies that have an increased affinity and/or a modified specificity for binding an antigen, wherein the modification of the antigen binding property results from an introduction of at least one mutation in an immunoglobulin chain variable region (V region) that changes the pattern of glycosylation in the V region. Such mutations may add a novel glycosylation site in the V region, change the location of one or more V region glycosylation site(s), or preferably remove a pre-existing V region glycosylation site, more preferably removing an N-linked glycosylation site in a V region framework, and most preferably removing an N-linked glycosylation site that occurs in the heavy chain V region framework in the region spanning about amino acid residue 65 to about amino acid residue 85, using the numbering convention of Co et al. (1992) op.cit.. In a preferred embodiment, the method of the invention does not substantially modify glycosylation of constant regions. A preferred method introduces V region mutations that increase the antibody affinity for specific antigen.

The present invention also provides mutant immunoglobulins with an altered antigen binding property, preferably glycosylation-reduced antibodies which have at least one V region glycosylation site removed by mutation. Preferably such mutant immunoglobulins include a mutated immunoglobulin heavy chain variable region, and more preferably include an entire mutated immunoglobulin heavy chain. In some embodiments, a mutant antibody will include at least one mutated heavy chain portion and at least one mutated light chain portion. In preferred embodiments, a mutant antibody will include at least one mutated full-length heavy chain and at least one mutated full-length light chain, wherein either or both heavy and light chain species may be naturally-occurring, chimeric, or humanized. Alternatively, in some embodiments it is preferred that mutated antibodies include a mutated heavy chain and an unmutated light chain, or vice versa.

A preferred embodiment of the invention is a mutant antibody that includes a glycosylation-reduced immunoglobulin chain, wherein at least one naturally-occurring V region glycosylation site, preferably at a position in the V region framework, has been removed by mutation. In some preferred embodiments, a glycosylation-reduced immunoglobulin chain is a heavy chain wherein at least one carbohydrate moiety is attached to a constant region amino acid residue through N-linked glycosylation.

This invention further provides sterile compositions of therapeutic immunoglobulins for treating disease in mammals, comprising a unit dosage of a mutant immunoglobulin, or a mixture of mutant immunoglobulins, having enhanced antigen binding properties.

BRIEF DESCRIPTION OF THE DRAWINGS

FIG. 1. Amino acid sequences of the third framework region of the chimeric and humanized heavy chain variable domains of the M195 antibodies, with and without glycosylation sites. The N-linked glycosylation site at amino acid positions 73–75 is underlined.

DEFINITIONS

Figure 2:
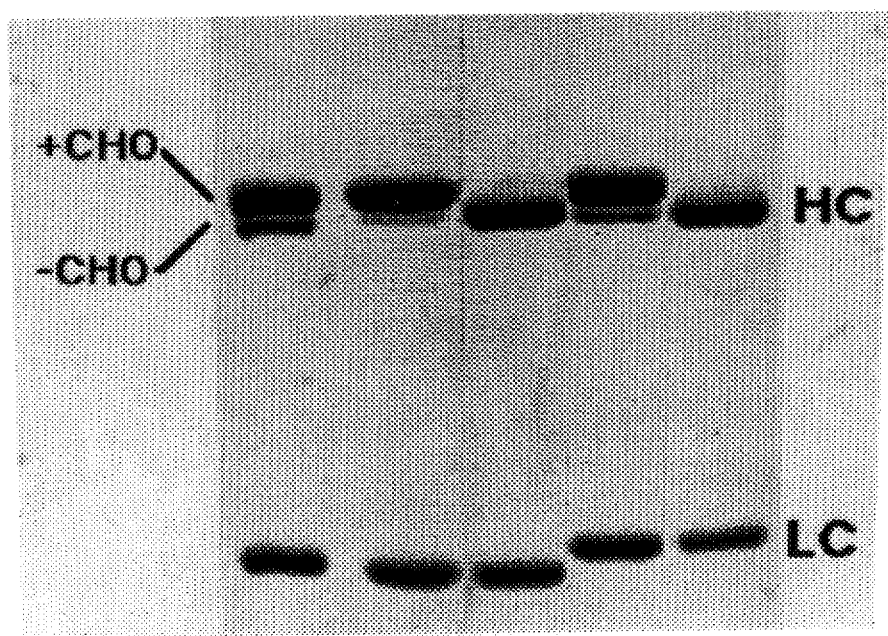
FIG. 2. SDS-PAGE analysis of the purified murine, chimeric and humanized M195 antibodies. Lane 1: murine; lane 2: chimeric; lane 3: chimeric(−)CHO; lane 4: humanized (+)CHO; lane 5: humanized. HC=heavy chain, LC=light chain, (+)CHO=glycosylated V region, (−)CHO= aglycosylated V region.

For purposes of the present invention, the following terms are defined below.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991) which is incorporated herein by reference).

"Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. The specific site of attachment is typically signaled by a sequence of amino acids, referred to herein as a "glycosylation site sequence". The glycosylation site sequence for N-linked glycosylation is: -Asn-X-Ser- or -Asn-X-Thr-, where X may be any of the conventional amino acids, other than proline. The predominant glycosylation site sequence for O-linked glycosylation is: -(Thr or Ser)-X-X-Pro- (SEQ. ID NO:1), where X is any conventional amino acid. The recognition sequence for glycosaminoglycans (a specific type of sulfated sugar) is -Ser-Gly-X-Gly- (SEQ. ID NO:2), where X is any conventional amino acid. The terms "N-linked" and "O-linked" refer to the chemical group that serves as the attachment site between the sugar molecule and the amino acid residue. N-linked sugars are attached through an amino group; O-linked sugars are attached through a hydroxyl group. However, not all glycosylation site sequences in a protein are necessarily glycosylated; some proteins are secreted in both glycosylated and nonglycosylated forms, while others are fully glysosylated at one glycosylation site sequence but contain another glycosylation site sequence that is not glycosylated. Therefore, not all glycosylation site sequences that are present in a polypeptide are necessarily glycosylation sites where sugar residues are actually attached. The initial N-glycosylation during biosynthesis inserts the "core carbohydrate" or "core oligosaccharide" (*Proteins, Structures and Molecular Principles*, (1984) Creighton (ed.), W. H. Freeman and Company, New York, which is incorporated herein by reference).

As used herein, "glycosylating cell" is a cell capable of glycosylating proteins, particularly eukaryotic cells capable of adding an N-linked "core oligosaccharide" containing at least one mannose residue and/or capable of adding an O-linked sugar, to at least one glycosylation site sequence in at least one polypeptide expressed in said cell, particularly a secreted protein. Thus, a glycosylating cell contains at least one enzymatic activity that catalyzes the attachment of a sugar residue to a glycosylating site sequence in a protein or polypeptide, and the cell actually glycosylates at least one expressed polypeptide. For example but not for limitation, mammalian cells are typically glycosylating cells. Other eukaryotic cells, such as insect cells and yeast, may be glycosylating cells.

As used herein, the term "antibody" refers to a protein consisting of one or more polypeptides substantially encoded by immunoglobulin genes. The recognized immunoglobulin genes include the kappa, lambda, alpha, gamma (IgG$_1$, IgG$_2$, IgG$_3$, IgG$_4$), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH—terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, and F(ab')$_2$, as well as bifunctional hybrid antibodies (e.g., Lanzavecchia et al., *Eur. J. Immunol.* 17, 105 (1987)) and in single chains (e.g., Huston et al., *Proc. Natl. Acad. Sci. U.S.A.*, 85, 5879–5883 (1988) and Bird et al., *Science*, 242, 423–426 (1988)). (See, generally, Hood et al., "Immunology", Benjamin, N.Y., 2nd ed. (1984), and Hunkapiller and Hood, *Nature*, 323, 15–16 (1986)). Thus, not all immunoglobulins are antibodies. (See, U.S. Ser. No. 07/634,278, filed 19 Dec. 1990, which is incorporated herein by reference, and Co et al. (1991) *Proc. Natl. Acad. Sci. (U.S.A.)* 88: 2869, which is incorporated herein by reference).

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., 4th Ed., U.S. Department of Health and Human Services, Bethesda, Md. (1987) and EP 0 239 400, both of which are incorporated herein by reference). The sequences of the framework regions of different light or heavy chains are relatively conserved within a species. As used herein, a "human framework region" is a framework region that is substantially identical (about 85% or more, usually 90–95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

It is well known that native forms of "mature" immunoglobulins will vary somewhat in terms of length by deletions, substitutions, insertions or additions of one or more amino acids in the sequences. Thus, both the variable and constant regions are subject to substantial natural modification, yet are "substantially identical" and still capable of retaining their respective activities. Human constant region and rearranged variable region DNA sequences can be isolated in accordance with well known procedures from a variety of human cells, but preferably immortalized B-cells. Similar methods can be used to isolate nonhuman immunoglobulin sequences from non-human sources. Suitable source cells for the DNA sequences and host cells for expression and secretion can be obtained from a number of sources, such as the American Type Culture Collection ("Catalogue of Cell Lines and Hybridomas," Fifth edition (1985) Rockville, Md., U.S.A., which is incorporated herein by reference).

In addition to these naturally-occurring forms of immunoglobulin chains, "substantially identical" modified heavy and light chains can be readily designed and manufactured utilizing various recombinant DNA techniques well known to those skilled in the art. For example, the chains can vary from the naturally-occurring sequence at the primary structure level by several amino acid substitutions, terminal and intermediate additions and deletions, and the like. Alternatively, polypeptide fragments comprising only a portion of the primary structure may be produced, which fragments possess one or more immunoglobulin activities (e.g., binding activity). In particular, it is noted that like many genes, the immunoglobulin-related genes contain separate functional regions, each having one or more distinct biological activities. In general, modifications of the genes encoding the desired epitope binding components may be readily accomplished by a variety of well-known techniques, such as site-directed mutagenesis (see, Gillman and Smith, *Gene* 8:81–97 (1979) and Roberts, S. et al., *Nature* 328:731–734 (1987), both of which are incorporated herein by reference). In preferred embodiments of the invention, the epitope binding component is encoded by immunoglobulin genes that are "chimeric" or "humanized" (see, generally, Co and Queen (1991) *Nature* 351:501, which is incorporated herein by reference).

"Chimeric antibodies" are antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant or effector domain from a human antibody (e.g., A.T.C.C. Accession No. CRL 9688 secretes an anti-Tac chimeric antibody), although other mammalian species may be used.

As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85–90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, mouse complementarity determining regions, with or without additional naturally-associated mouse amino acid residues, can be introduced into human framework regions to produce humanized immunoglobulins capable of binding to the CD33 antigen at affinity levels stronger than about $10^7 M^{-1}$. These humanized immunoglobulins will also be capable of blocking the binding of the CDR-donating mouse monoclonal antibody to CD33. These humanized immunoglobulins may be utilized alone in substantially pure form, or together with a chemotherapeutic agent such as cytosine arabinoside or daunorubicin active against leukemia cells, or complexed with a radionuclide such as iodine-131. In this particular example, all of these compounds will be particularly useful in treating leukemia and myeloid cell-mediated disorders.

As used herein, the terms "mutant antibody" and "mutationally-altered antibody" refers to an antibody that comprises at least one immunoglobulin variable region containing at least one mutation that modifies a V region glycosylation site. The word "mutant", as used herein, is interchangeable with "mutationally-altered" and "glycosylation site altered". A mutant immunoglobulin refers to an immunoglobulin (e.g., F(ab')$_2$, Fv, Fab, bifunctional antibodies, antibodies, etc.) comprising at least one immunoglobulin variable region containing at least one mutation that modifies a V region glycosylation site. A mutant immunoglobulin chain has at least one mutation that modifies a V region glycosylation site, typically in the V region framework. Thus, the pattern (i.e., frequency and or location(s) of occurrence) of V region glycosylation sites is altered in a mutant immunoglobulin A "V region glycosylation site" is a position in a variable region where a carbohydrate, typically an oligosaccharide, is attached to an amino acid residue in the polypeptide chain via an N-linked or O-linked covalent bond. Since not all glycosylation site sequences are necessarily glycosylated in a particular cell, a glycosylation site is defined operationally by reference to a designated cell type in which glycosylation occurs at the site, and is readily determined by one of ordinary skill in the art. Thus, a mutant antibody has at least one mutation that adds, subtracts, or relocates a V region glycosylation site, such as, for example, an N-linked glycosylation site sequence. Preferably, the mutation(s) are substitution mutations that introduce conservative amino acid substitutions, where possible, to modify a glycosylation site. Preferably, when the parent immunoglobulin sequence contains a glycosylation site in a V region framework, particularly in a location near the antigen binding site (for example, near a CDR), the glycosylation site sequence is mutated (e.g., by site-directed mutagenesis) to abolish the glycosylation site sequence, typically by producing a conservative amino acid substitution of one or more of the amino acid residues comprising the glycosylation site sequence. When the parent immunoglobulin sequence contains a glycosylation site in a CDR, and where the parent immunoglobulin specifically binds an epitope that contains carbohydrate, that glycosylation site is preferably retained. If the parent immunoglobulin specifically binds an epitope that comprises only polypeptide, glycosylation sites occuring in a CDR are preferably eliminated by mutation (e.g., site-directed mutation).

"Glycosylation-reduced antibodies" and "glycosylation-reduced immunoglobulin chains" are mutant antibodies and mutant immunoglobulin chains, respectively, in which at least one glycosylation site that is present in the parent sequence has been destroyed by mutation and is absent in the mutant sequence.

"Glycosylation-supplemented antibodies" and "glycosylation-supplemented immunoglobulin chains" are mutant antibodies and mutant immunoglobulin chains, respectively, in which at least one glycosylation site is present in the mutant sequence at a position where no glycosylation site occurs in the parent sequence. Typically, glycosylation-supplemented antibodies that have a higher binding affinity for a carbohydrate-containing epitope than does the parent antibody have a glycosylation site present in a CDR where the parent antibody does not. Typically, a glycosylation-supplemented antibody that specifically binds an epitope that contains polypeptide sequence but no carbohydrate have a lower affinity that the parental antibody.

For example, but not for limitation, a mutant immunoglobulin of the invention may comprise part or all of a heavy chain and part or all of a light chain, or may comprise only part or all of a heavy chain. However, a mutant immunoglobulin must contain a sufficient portion of an immunoglobulin superfamily gene product so as to retain the property of binding to a specific antigen target, or epitope with an affinity of at least $1\times10^7 M^{-1}$.

It is understood that the mutant immunoglobulins designed by the present method may have additional conservative amino acid substitutions which have substantially no effect on antigen binding or other immunoglobulin functions. Conservative amino acid substitution is a substitution of an amino acid by a replacement amino acid which has similar characteristics (e.g., those with acidic properties: Asp and Glu). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). By conservative substitutions is intended combinations such as, for example: gly, ala; val, ile, leu; asp, glu; asn, gln; ser, thr; lys, arg; and phe, tyr.

"Parent immunoglobulin sequence" (or "parent immunoglobulin") and "parent polynucleotide sequence" refer herein to a reference amino acid sequence or polynucleotide sequence, respectively. A parent polynucleotide sequence may encode a naturally-occurring immunoglobulin chain, a chimetic immunoglobulin chain, or a humanized immunoglobulin chain, wherein glycosylation site sequences, if any, present in the V region occur about at the same relative amino acid residue position(s) at which glycosylation site sequence(s) are present in naturally-occurring immunoglobulin sequence(s) from which the parent sequence(s) were derived. When mutations, such as site-directed mutations, are introduced into a parent immunoglobulin sequence, the resultant sequence is referred to as a mutant immunoglobulin sequence (or a mutated immunoglobulin sequence).

DETAILED DESCRIPTION

In accordance with the present invention, mutant immunoglobulins, methods to produce such mutant immunoglobulins, pharmaceutical compositions of mutant immunoglobulins, therapeutic uses of such mutant immunoglobulins, and methods and compositions for using mutant immunoglobulins in diagnostic and research applications are provided.

In accordance with the present invention, novel mutant immunoglobulins capable of specifically binding to predetermined antigens with strong affinity are provided. These immunoglobulins are substantially non-immunogenic in humans but have binding affinities of at least about $10^8 M^{-1}$, preferably $10^9 M^{-1}$ to $10^{10} M^{-1}$, or stronger. These mutant immunoglobulins are characterized by the presence of a mutation in a V region amino acid sequence that changes the glycosylation pattern(s) of the mutant variable region when the immunoglobulin is expressed in a host that is competent to conduct post-translational glycosylation, particularly N-linked glycosylation at N-linked glycosylation site sequences.

Glycosylation at a variable domain framework residue can alter the binding interaction of the antibody with antigen. The present invention includes criteria by which a limited number of amino acids in the framework or CDRs of a humanized immunoglobulin chain are chosen to be mutated (e.g., by substitution, deletion, or addition of residues) in order to increase the affinity of an antibody.

Affinity for binding a pre-determined polypeptide antigen can generally be increased by introducing mutations into the V region framework, typically in areas adjacent to one or more CDRs and/or in a framework region spanning from about amino acid residue 65 to about amino acid residue 85, so that one or more, preferably all, pre-existing glycosylation site sequences are removed. A mutation is adjacent to a CDR if it is within about 5 to 10 amino acids of a CDR-framework boundary, typically within 8 amino acids of a CDR-framework boundary. Typically, such mutation(s) involves the introduction of conservative amino acid substitutions that destroy the glycosylation site sequence(s) but do not substantially affect the hydropathic structural properties of the polypeptide. Typically, mutations that introduce a proline residue are avoided. It is preferable to introduce mutations that destroy N-linked glycosylation site sequences, although O-linked glycosylation site sequences may be targeted as well.

Mutations of the invention are typically produced by site-directed mutation using one or more mutagenic oligonucleotide(s) according to methods known in the art and described in Maniatis et al., *Molecular Cloning: A Laboratory Manual*, 2nd Ed., (1989), Cold Spring Harbor, N.Y. and Berger and Kimmel, *Methods in Enzymology, Volume 152, Guide to Molecular Cloning Techniques* (1987), Academic Press, Inc., San Diego, Calif., which are incorporated herein by reference. Such mutations may include substitutions, additions, deletions, or combinations thereof.

The nucleic acid sequences of the present invention capable of ultimately expressing the desired mutant antibodies can be formed from a variety of different polynucleotides (genomic or cDNA, RNA, etc.) by a variety of different techniques. Joining appropriate genomic sequences is presently the most common method of production, but cDNA and synthetic sequences may also be utilized (see, European Patent Application Nos. 85102655.8, 85305604.2, 84302368.0 and 85115311.4, as well as PCT Application Nos. GB85/00392 and US86/02269, all of which are incorporated herein by reference).

The DNA constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In general, prokaryotes can be used for cloning the DNA sequences encoding a mutant antibody. *E. coli* is one prokaryotic host particularly useful for cloning the DNA sequences of the present invention. Particular *E. coli* strains that can be used include, HB101, DH-1, and MH-1. Other microbial hosts suitable for use include bacilli, such as *Bacillus subtilus*, and other enterobacteriaceae, such as Salmonella, Serratia, and various Pseudomonas species.

Other microbes, such as yeast may be used for expression. Saccharomyces is a preferred yeast host capable of post-translational glycosylation, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utilization.

When constructing vectors for use in yeast, the plasmid YRp7 can be used (see, Stinchcomb, et al., *Nature*, 282:39 (1979)). This plasmid contains the trp1 gene which is a selectable marker for a mutant strain which lacks the ability to grow on media containing tryptophan. The presence of the trp1 gene allows transformed mutant cells to grow on selective media and to be identified.

In addition to eukaryotic microorganisms such as yeast, mammalian tissue cell culture may also be used to produce the polypeptides of the present invention (see, Winnacker, "From Genes to Clones, "VCH Publishers, N Y., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, myeloma cell lines, etc, but preferably transformed B-cells or hybridomas. Expression vectors for these cells can include expression control sequences, such as an origin of replication, a promoter, an enhancer (Queen, c. et al., *Immunol. Rev.* 89:49–68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300 bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment or electroporation may be used for other cellular hosts. Other methods used to transform mammalian cells include the use of Polybrene, protoplast fusion, liposomes, electroporation, and microinjection (see, generally, Sambrook et al., supra).

Once expressed, mutant antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, R., *Protein Purification*, Springer-Verlag, N.Y. (1982)). Once purified, partially or to homogeneity as desired, the polypeptides may then be used therapeutically or in developing and performing assay procedures, immunofluorescent stainings, and the like (see, generally, *Immunological Methods*, Vols. I and II, Eds. Lefkovits and Pernis, Academic Press, New York, N.Y. (1979 and 1981)).

The mutant immunoglobulins of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens well known to those skilled in the art. For treatment of autoimmune disease, the antibodies will typically bind to an antigen expressed on T-cells, such as CD4, the IL-2 receptor, the various T-cell antigen receptors and many other antigens well known to those skilled in the art (e.g., see *Fundamental Immunology*, 2nd ed., W. E. Paul, ed., Raven Press: New York, N.Y., which is incorporated herein by reference). For treatment of viral infections, the antibodies will typically bind to an antigen expressed on cells infected by a particular virus such as the various glycoproteins (e.g., gB, gD, gH) of herpes simplex virus and cytomegalovirus, and many other antigens well known to those skilled in the art (e.g., see *Virology*, 2nd ed., B. N. Fields et al., eds., (1990), Raven Press: New York, N.Y., which is incorporated herein by reference).

Pharmaceutical compositions comprising mutant antibodies of the present invention are useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the mutant antibodies in these formulations can vary widely, i.e., from less than about 0.01%, usually at least about 0.1% to as much as 5% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and about 1 mg of mutant antibody. A typical composition for intravenous infusion can be made up to contain 250 ml of sterile Ringer's solution, and 10 mg of mutant antibody. Actual methods for preparing parenterally administrable compositions will be known or apparent to those skilled in the art and are described in more detail in, for example, *Remington's Pharmaceutical Science*, 15th Ed., Mack Publishing Company, Easton, Pa. (1980), which is incorporated herein by reference.

The mutant antibodies of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present mutant antibodies or a cocktail thereof can be administered for prophylactic and/or therapeutic treatments. In therapeutic application, compositions are administered to a patient already affected by the particular disease, in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.01 to about 100 mg of mutant antibody per dose, with dosages of from 1 to 10 mg per patient being more commonly used.

In prophylactic applications, compositions containing the mutant antibodies or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 0.1 to 100 mg per dose, especially 1 to 10 mg per patient.

Single or multiple administrations of the compositions can be carried out with dose levels and pattern being selected by the treating physician. In any event, the pharmaceutical formulations should provide a quantity of the mutant antibodies of this invention sufficient to effectively treat the patient.

Kits can also be supplied for use with the subject mutant antibodies in the protection against or detection of a cellular activity or for the presence of a selected cell surface receptor or the diagnosis of disease. Thus, the subject composition of the present invention may be provided, usually in a lyophilized form in a container, either alone or in conjunction with additional antibodies specific for the desired cell type. The mutant antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the mutant antibody is employed in an assay, this will usually be present in a separate vial. The second antibody is typically conjugated to a label and formulated in an analogous manner with the antibody formulations described above. The mutant antibodies can be used in ELISA assays, and other immunologic assays well known to those skilled in the art, in order to increase sensitivity or reduce background.

The following examples are offered by way of illustration, not by way of limitation.

EXPERIMENTAL EXAMPLES

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., 1989. Other general references are provided throughout this document. The procedures therein are believed to be well known in the art and are provided for the convenience of the reader. All the information contained therein is incorporated herein by reference.

Recombinant DNA technology was used to humanize M195 by cembining the complementarity determining regions of the murine M195 antibody with the framework and constant regions of a human antibody. Surprisingly, the humanized M195 antibody has a several-fold higher binding affinity for the CD33 antigen that the original murine antibody.

The chimeric and humanized M195 antibodies exhibited improved effector functions, as expected, but the humanized antibody also showed an unexpected increase in binding affinity to the CD33 antigen (Co et al., op.cit.). The increase in binding affinity results directly from the removal of an N-linked glycosylation site at heavy chain V region framework position 73 of the humanized M195 antibody. Removing that glycosylation site from the murine M195 variable domain, without humanizing the antibody, leads to the same increase in affinity.

Materials and Methods

Construction of antibody variants

To construct the glycosylated humanized and aglycosylated chimeric M195 antibodies, the genes for the respective variable domains were modified by site-directed mutagenesis (Maniatis et al., *Molecular Cloning: A Laboratory Manual*, 2nd Ed., (1989), Cold Spring Harbor, N.Y. and Berger and Kimmel, *Methods in Enzymology, Volume 152, Guide to Molecular Cloning Techniques* (1987), Academic Press, Inc., San Diego, Calif., which are incorporated herein by reference). The modified genes were inserted in the pVgl expression vector and transfected into Sp2/0 cells together with the respective light chain containing vectors, as described (Co et al., op.cit.). Antibody-producing clones were selected, and antibody purified by protein A chromatography, as described (Co et al., op.cit.).

Affinity measurements

Murine M195 antibody was labeled with Na-$^{125}$I using chloramine-T, to 2–10 mCi/mg protein. Relative affinity of the various M195 constructs was measured by competitive binding with the $^{125}$I-M195 antibody. Specifically, increasing amounts of cold competitor antibody were incubated with $2\times10^5$ HL60 cells and 50 ng $^{125}$I-M195 in 200 ul RPMI plus 2% human serum for 1 hr at 0° C. Cells were washed twice in RPMI and counted. The assays were done in the presence of human serum to avoid nonspecific FcR binding.

Results

While the chimeric M195 antibody has binding affinity for the CD33 antigen indistinguishable from the murine antibody, which provided the V region, competitive binding measurements show that the humanized M195 antibody has about an 8-fold higher affinity (see below). Since the only difference between the chimeric and humanized antibodies is the amino acid sequence of the V domain, the structural basis for the affinity differences resides in this region. Examination of the sequence of the murine (or chimeric) heavy chain V region (FIG. 1) reveals that it contains the amino acid sequence -Asn-Ser-Ser- starting at position 73, which is an example of the -Asn-Xaa-(Ser/Thr)- recognition sequence for N-linked glycosylation (following the convention that amino acid sequences are read in the orientation amino-terminal to carboxy-terminal). In contrast, the humanized $V_H$ region (FIG. 1), which utilizes the framework of the human Eu antibody (Co et al., op.cit.), does not have this or any -Asn-Xaa-(Ser/Thr)- glycosylation sequence.

While an -Asn-Xaa-(Ser/Thr)- sequence is necessary for N-linked glycosylation, not all such sequences are actually glycosylated. To determine if glycosylation at Ash 73 actually occurs and whether it affects the antibody binding affinity, this glycosylation site sequence was removed from the chimeric M195 antibody and a similar glycosylation site sequence was introduced into the humanized antibody. To remove the site from the $V_H$ region of the chimeric antibody, the Asn codon at position 73 was changed to a Gln codon. To introduce a potential glycosylation site into the $V_H$ region of the humanized antibody, the sequence in position 73–76 was changed from -Glu-Ser-Thr-Asn- (SEQ. ID NO:3) to the sequence -Asn-Ser-Ser-Ser- (SEQ. ID NO:4) that occurs in the chimeric $V_H$ region. Residues 73–75 represent the -Asn-X-(Ser/Thr)- glycosylation signal, while residue 76 was replaced because it has been reported that the amino acid immediately after the glycosylation site can affect the extent of glycosylation (Gavel and Heijne, *Protein Engineering* 3:433 (1990)). These amino acid alternations were achieved by site-directed mutagenesis of the respective genes. The altered $V_H$ region sequences were inserted into heavy chain expression plasmids, which were then transfected into Sp2/0 cells together with the respective light chain containing plasmids.

Antibodies purified from the original murine M195 hybridoma and from the transfectants were analyzed by SDS-PAGE (FIG. 2). Under reducing conditions, the heavy and light chains of the various antibody constructs respectively migrate as bands of approximately 50 kDa and 25 kDa. The light chains of the chimeric and humanized antibodies migrate slightly differently because of the differing compositions of their $V_L$ domains. The heavy chains of the forms of the chimeric and humanized antibodies with potential $V_H$ glycosylation sites (FIG. 2, lanes 2 and 4) comigrate with the murine heavy chains (lane 1), while the heavy chains of the forms without potential $V_H$ glycosylation sites migrate slightly faster (lanes 3 and 5). Since the only amino acid differences between the two forms of the chimeric antibodies, and respectively between the two forms of the humanized antibodies, are the changes introduced at the glycosylation site, the most plausible interpretation of the mobility shifts is that the forms with the site migrate more slowly because of an attached carbohydrate group. Moreover, for the three heavy chains with the $V_H$ glycosylation site (lanes 1, 2 and 4), there is a small lower band comigrating with the heavy chains without the site (lanes 3 and 5), suggesting that a small portion of the heavy chain in these antibodies (about 10–20%) is not properly glycosylated at Asn 73. The appearance of heavy chain doublets in SDS-PAGE analysis of monoclonal antibodies has often been observed before, and is now shown to result from heterogeneity in glycosylation of the $V_H$ region.

Figure 3A:
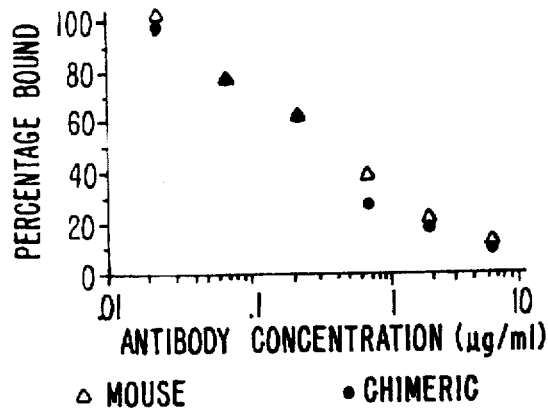
FIG. 3. Competitive binding of M195 antibodies to HL60 cells. (A) Chimeric and murine, (B) humanized and murine, (C) aglycosylated chimeric and humanized, (D) glycosylated humanized and murine.
Figure 3B:
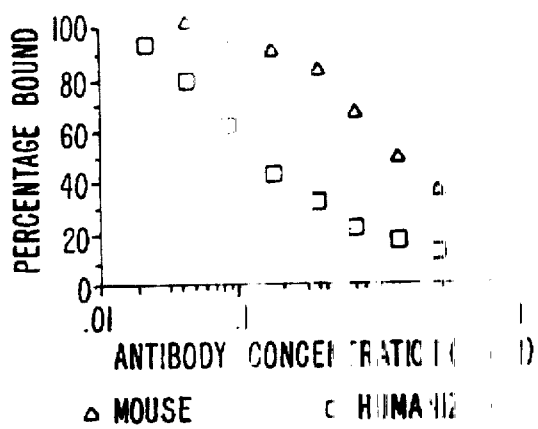
Figure 3C:
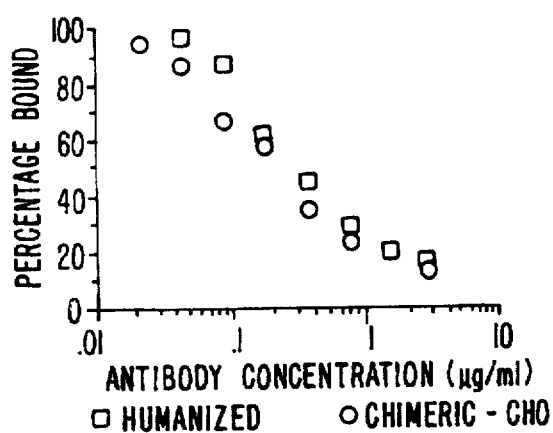
Figure 3D:
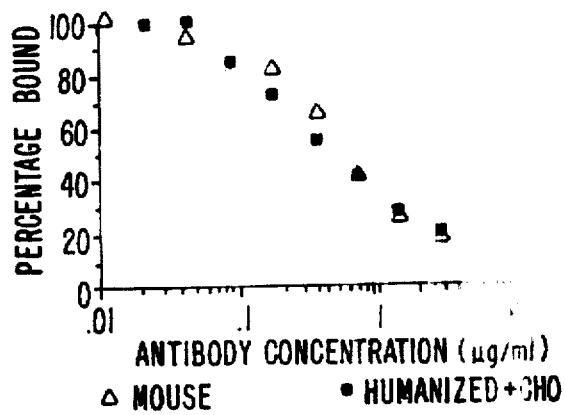

Direct binding of iodinated antibodies to determine affinity constants may be inaccurate, due to iodine atoms introduced into the binding region or denaturation during radiolabeling. Therefore, to accurately compare the binding affinities of the various antibody constructs, the unlabeled antibodies were allowed to compete with iodinated murine M195 for binding to HL60 cells, which express the CD33 antigen. Human serum, containing human IgG, was present in the reactions to inhibit non-specific and Fc receptor binding. The binding affinity of murine M195 has previously been measured as $2\times10^9 M^{-1}$ by Scatchard analysis (Co et al., *J. Immunol.* (op.cit.), and the same value was obtained from the competition of unlabeled murine M195 with iodinated M195 (FIG. 3A). The chimeric M195 antibody competes with the same efficiency as murine M195 (FIG. 3A), giving an affinity of $2\times10^9$. This is consistent with expectation, since the chimeric antibody has the same V domain as the murine antibody. However, the humanized M195 antibody competed more effectively that the chimeric (or murine) antibody, displaying an about 8-fold increase in binding affinity (FIG. 3B). The chimeric antibody from which the $V_H$ glycosylation site had been removed competed as well as the humanized M195 antibody (FIG. 3C), that is, elimination of the glycosylation site increased the binding affinity 8-fold. Conversely, the humanized antibody into which we re-introduced a glycosylation site at Asn 73 competed with similar affinity as the original mouse antibody, showing that glycosylation decreased the binding affinity (FIG. 3D).

Natural glycosylation at Asn 73 of the M195 antibody reduces binding affinity for the CD33 antigen by 8-fold, and the lost affinity may be recovered by removal of the recognition sequence for carbohydrate attachment (i.e., the V region glycosylation site sequence).

---

We claim:

1. A method for producing a mutant antibody that comprises a mutant immunoglobulin chain, the mutant antibody having higher affinity for an antigen than a parent antibody that comprises a parent immunoglobulin chain, the method comprising the steps of:

introducing at least one mutation into a parent polynucleotide that encodes the parent immunoglobulin chain to produce a mutant polynucleotide that encodes the mutant immunoglobulin chain, the mutation introducing into the mutant immunoglobulin chain an amino acid substitution that eliminates a variable region framework glycosylation site of the parent immunoglobulin chain; and expressing the mutant polynucleotide in a cell as the mutant immunoglobulin chain so as to produce the mutant antibody.

2. The method of claim 1 wherein the glycosylation site is an N-linked glycosylation site selected from the group consisting of:

(1) -Asn-X-Ser-; and (2) -Asn-X-Thr-;

wherein X is an amino acid other than Pro.

3. The method of claim 1 wherein the glycosylation site is an O-linked glycosylation site selected from the group consisting of:

(1) -Thr-X-X-Pro-; and (2) -Ser-X-X-Pro-;

wherein X is an amino acid.

4. The method of claim 1 wherein the mutant antibody is a humanized version of the parent antibody.

5. The method of claim 1 wherein the mutant polynucleotide encodes a mutant immunoglobulin chain whose variable region framework has no glycosylation sites.

6. The method of claim 1 wherein the mutant polynucleotide encodes a mutant immunoglobulin chain whose variable region framework has no N-linked glycosylation sites.

7. The method of claim 1 wherein the parent antibody is murine M195 antibody.

8. The method of claim 1 wherein the mutant antibody is a humanized M195 antibody.

9. The method of claim 1 wherein the antigen is a cell surface glycoprotein.

10. The method of claim 1 wherein the mutant immunoglobulin chain is an immunoglobulin heavy chain.

11. The method of claim 1 wherein the amino acid substitution is a conservative amino acid substitution.

12. The method of claim 2 wherein the mutant immunoglobulin chain is an immunoglobulin heavy chain.

13. The method of claim 2 wherein the amino acid substitution is a conservative amino acid substitution.

14. The method of claim 3 wherein the mutant immunoglobulin chain is an immunoglobulin heavy chain.

15. The method of claim 3 wherein the amino acid substitution is a conservative amino acid substitution.

16. The method of claim 9 wherein the cell surface glycoprotein is the CD33 antigen.

* * * * *